United States Patent [19]

Cale, Jr.

[11] 4,379,151
[45] Apr. 5, 1983

[54] 3-PHENOXYAZETIDINES FOR ANOREXIGENIC ACTIVITY

[75] Inventor: Albert D. Cale, Jr., Mechanicsville, Va.

[73] Assignee: A. H. Robins Company, Inc., Richmond, Va.

[21] Appl. No.: 312,046

[22] Filed: Oct. 16, 1981

Related U.S. Application Data

[63] Continuation-in-part of Ser. No. 886,487, Mar. 14, 1978, abandoned.

[51] Int. Cl.³ .................. C07D 205/04; A61K 31/395
[52] U.S. Cl. .................. 424/244; 260/239 A
[58] Field of Search .................. 424/244

[56] References Cited

U.S. PATENT DOCUMENTS 4,226,861  10/1980  Cale, Jr. .................. 424/244

FOREIGN PATENT DOCUMENTS 1425238  2/1976  United Kingdom .

OTHER PUBLICATIONS

Testa et al., Research Progress in Organic-Biological and Medicinal Chemistry, vol. 1, p. 510 (1964).

Primary Examiner—Mark L. Berch

[57] ABSTRACT

3-Phenoxyazetidines having the formula:

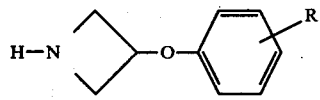

wherein R is hydrogen, aminocarbonyl and trifluoromethyl having anorexigenic activity are disclosed.

4 Claims, No Drawings

3-PHENOXYAZETIDINES FOR ANOREXIGENIC ACTIVITY

This application is a continuation-in-part application of copending U.S. patent application Ser. No. 886,487 filed Mar. 14, 1978, now abandoned.

BACKGROUND OF THE INVENTION

1. Field of the Invention

The present invention relates to certain novel heterocyclic compounds and more particularly to 3-phenoxyazetidines, compositions thereof, and methods of making and using same.

2. Description of the Prior Art

German Offenlegungsschrift No. 2.317.980 discloses N-oxides of N-substituted azetidine compounds and their use as intermediates for the preparation of 2-substituted isoxazolidines.

SUMMARY OF THE INVENTION

The invention is especially concerned with novel 3-phenoxyazetidine compounds having the formula:

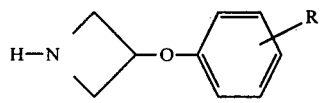

Formula I wherein;

R is hydrogen, aminocarbonyl and trifluoromethyl, and pharmaceutically acceptable acid addition salts thereof.

The compounds of Formula I are useful because of their pharmacological action on the central nervous system. In particular, the compounds have anorexigenic activity.

The anorexigenic property was determined according to the procedure of Roszkowski and Kelly, A Rapid Method for Assessing Drug Inhibition, J. Pharmacol. Exptl. Therap. 140, 367-374 (1963) as modified by Alphin and Ward, Anorexigenic Effects of Fenfluramine Hydrochloride in Rats, Guinea Pigs and Dogs, Toxicology and Applied Pharmacology 14, 182-191 (1969). Among the compounds of the present invention which have shown good activity in the aforementioned test is the representative compound 3-phenoxyazetidine.

It is, therefore, an object of the present invention to provide certain novel 3-phenoxyazetidines, compositions thereof, and methods of making and using the same. Another object is to provide novel 3-phenoxyazetidines having anorexigenic activity. Other objects of the invention will be apparent to one skilled in the art and still other objects will become apparent hereinafter.

This invention also includes pharmaceutically acceptable acid addition salts of the compounds of Formula I. Such acid addition salts are easily prepared by methods known in the art and can be derived from various organic and inorganic acids such as citric, acetic, lactic, maleic, fumaric, benzoic, tartaric, ascorbic, pamoic, succinic, methanesulfonic, malic, citraconic, itaconic acid, hydrochloric, hydrobromic, sulfuric, phosphoric, nitric and related acids.

The compounds of the present invention may be conveniently prepared by contacting the appropriate 1-$R^1$-3-phenoxyazetidine of the formula:

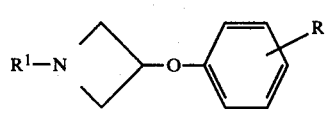

wherein R is defined as hereinbefore and $R^1$ is α-methylbenzyl or diphenylmethyl with hydrogen in the presence of palladium on charcoal catalyst. The hydrogenolysis is carried out in the presence of a lower alkanol solvent, ethanol being preferred. The rate of hydrogenolysis is dependent somewhat on time and temperature, a higher temperature generally decreasing the time required for complete hydrogenolysis. Typical times vary from about 3 hours to about 24 hours with typical temperature varying from about 70° C. to about 90° C.

The starting material of Formula II is conveniently prepared by contacting a 1-$R^1$-3-azetidinol of the formula:

wherein $R^1$ is defined as hereinbefore with the appropriate fluorobenzene of the formula:

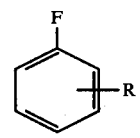

wherein R is hydrogen, chloro and trifluoromethyl. The reaction is run at a temperature of from about 80° C. to about 100° C. and for a period of from about two hours to about five hours. The preferred solvent is dimethylformamide. The starting material of Formula II wherein R is aminocarbonyl is preferably prepared by basic hydrolysis of a precursor cyano compound.

The compounds of Formula I and Formula II are basic compounds and are useful for neutralizing acidic solutions.

The following preparations and examples describe in detail compounds illustrative of the present invention and methods which have been devised for their preparation. It will be apparent to one skilled in the art that many modifications, both of materials and methods, may be practiced without departing from the purpose and intent of the disclosure.

PREPARATION 1

3-(3-Chlorophenoxy)-1-(α-methylbenzyl)azetidine Oxalate 1-(α-Methylbenzyl)-3-hydroxyazetidine maleate (393 g., 1.3 moles) was partitioned in dilute potassium hydroxide-benzene. The separated dried benzene solution was concentrated, the residual oil dissolved in 250 ml. of dimethylformamide and added dropwise to a stirred suspension of 53 g. (1.1 moles) of 50% sodium hydride in 750 ml. of dimethylformamide at 90° C. The mixture was heated at 90° C. for 1 hr. and 130.5 g. (1 mole) of 3-chlorofluorobenzene added dropwise at 90° C. The mixture was refluxed for 3 hrs., cooled and partitioned between isopropyl ether and dilute sodium hydroxide.

The isopropyl ether solution was dried, concentrated, and the residue added to 1200 ml. of isopropyl alcohol containing 90 g. (1 mole) of oxalic acid. The oxalate salt was recrystallized from ethanol. Yield 263 g. (69%); m.p. 141°–144° C.

Analysis: Calculated for $C_{19}H_{20}ClNO_5$: C,60.40; H,5.34; N,3.71. Found: C,60.19; H,5.55; N,3.60

PREPARATION 2

1-(α-Methylbenzyl)-3-(4-trifluoromethylphenoxy)azetidine

The maleate salt of 1-(α-methylbenzyl)-3-hydroxyazetidine (78.6 g., 0.20 mole) was partitioned between benzene and dilute sodium hydroxide, the benzene layer dried, filtered, and concentrated at reduced pressure. The residue was dissolved in 100 ml. of dry dimethylformamide and added at a rapid dropwise rate, to a stirring suspension of 10.1 g. (0.22 mole) of sodium hydride (50% in mineral oil) in 150 ml. of dry dimethylformamide at 90° C. The solution was heated at 90° C. for one hour and then treated dropwise with 32.0 g. (0.20 mole) of 4-trifluoromethylfluorobenzene. The solution was refluxed for three hours. The cooled solution was partitioned between water and isopropyl ether, and the ether layer extracted with dilute hydrochloric acid. The aqueous acid layer was made basic with concentrated sodium hydroxide and ice, and extracted with isopropyl ether. The ether layer was concentrated and the residue distilled at 150°–160° C./0.2 mm. to give 25.6 g. of product.

Analysis: Calculated for $C_{18}H_{18}F_3NO$: C,67.28; H,5.65; N,4.36 Found: C,67.27; H,5.84; N,4.34

Preparations 3 to 7 were prepared according to the procedures set forth in detail in Preparations 1 to 2 by reacting 1-(α-methylbenzyl)-3-azetidinol with the appropriately substituted fluorobenzene. The physical constants are shown in Table I.

TABLE I $C_6H_5(CH_3)CH-N\underset{}{\bigtriangleup}-O-\underset{}{\bigcirc}-R$

| Preparation | R | M.P. (b.p.) °C. | Salt |
|---|---|---|---|
| 3 | 2-CONH$_2$ | 148–52 | — |
| 4 | 4-CN | 65–8 | — |
| 5 | 3-CF$_3$ | 150–3 | (COOH)$_2$ |
| 6 | 2-CF$_3$ | 162–3 | (COOH)$_2$ |
| 7 | 3-CN | 1(185–90) | — |

[1] At 0.2 mm.

The analytical data of Preparations 3 to 7 are shown in Table II.

TABLE II

| | Analytical Data on Preparations 3 to 7 | | | | | |
|---|---|---|---|---|---|---|
| | Empirical | Calculated | | | Found | |
| Preparation | Formula | C | H | N | C | H | N |
| 3 | $C_{18}H_{20}N_2O_2$ | 72.95 | 6.80 | 9.45 | 72.56 | 6.78 | 9.32 |
| 4 | $C_{18}H_{18}N_2O$ | 77.67 | 6.52 | 10.06 | 77.61 | 6.53 | 10.01 |
| 5 | $C_{20}H_{20}F_3NH_5$ | 58.39 | 4.90 | 3.41 | 57.99 | 4.97 | 3.39 |
| 6 | $C_{20}H_{20}F_3NO_5$ | 58.39 | 4.90 | 3.41 | 58.15 | 4.89 | 3.37 |
| 7 | $C_{18}H_{18}N_2O$ | 77.67 | 6.52 | 10.06 | 77.32 | 6.54 | 9.87 |

PREPARATION 8

3-[1-(α-Methylbenzyl)-3-azetidinyloxy]benzamide Oxalate

3-[1-(α-Methylbenzyl)-3-azetidinyloxy]benzonitrile (50.0 g.; 0.18 mole) in 500 ml. of t-butyl alcohol was treated with 50.0 g. of finely ground potassium hydroxide. The mixture was stirred at reflux for 30 min. Ice and water were added to the reaction mixture and the organic layer was separated and dried over sodium sulfate. The dried filtered solution was concentrated at reduced pressure. The residue was dissolved in methanol and treated with an equivalent of oxalic acid, and the oxalate salt was recrystallized from ethanol to give 11.4 g. (16%) of product, (m.p. 145° C.).

Analysis: Calculated for $C_{20}H_{22}N_2O_6$: C,62.17; H,5.74; N,7.25 Found: C,62.17; H,5.80; N,7.20

PREPARATION 9

4-[1-(α-Methylbenzyl)-3-azetidinyloxy]benzamide

To 45.0 g. (0.16 mole) of 3-[1-(α-methylbenzyl)-3-azetidinyloxy]benzonitrile in 500 ml. of t-butyl alcohol was added 45.0 g. of finely ground potassium hydroxide. The mixture was stirred and refluxed for 30 minutes. Ice and water were added and a thick white solid separated. The solid was recrystallized from toluene to give 30.0 g. (63%) of product melting at 174°–178° C.

Analysis: Calculated for $C_{18}H_{20}N_2O_2$: C,72.05; H,6.80; N,9.45 Found: C,73.06; H,6.79; N,9.44

PREPARATION 10

1-Diphenylmethyl-3-phenoxyazetidine

To a stirred suspension of 8.6 g. (0.22 mole) of sodium amide in 100 ml. of dry toluene was added 18.2 g. (0.2 mole) of phenol in 50 ml. of dry toluene. After stirring for 2 hrs. at 60° C. the pot temperature was raised to 80° C. and a solution of 1-diphenylmethyl-3-methylsulfonyloxyazetidine (63.4 g.; 0.2 mole) in 200 ml. of dry toluene was added dropwise. After an additional 2 hrs. at 80° C. the cooled mixture was treated with water, the toluene layer was extracted with dilute sodium hydroxide solution, dried and concentrated at reduced pressure. The residue was crystallized twice from a water-isopropanol mixture. The free base melted at 83°–85° C.

Analysis: Calculated for $C_{22}H_{21}NO$: C,83.78; H,6.71; N,4.44 Found: C,83.69; H,6.81; N,4.41

EXAMPLE 1

3-(Phenoxy)azetidine Methanesulfonate

A 200 ml. solution of 7.8 g. (0.025 mole) of 1-diphenylmethyl-3-phenoxyazetidine in ethanol was treated with 20% Pd (OH)$_2$ on carbon and hydrogenated for 23 hr. at about 45 psi and 80° C. The mixture was filtered and the filtrate concentrated. The residue was diluted to 30 ml. with ethanol and 2.5 g. of methanesulfonic acid added. The isolated methanesulfonate salt was recrystallized from ethanol. The salt weighed 2.3 g. (37.5%) and melted at 128°–130° C.

Analysis: Calculated for $C_{10}H_{15}NO_4S$: C,48.97; H,6.16; N,5.71 Found: C,48.40; H,6.19; N,5.63

The compound was also prepared by hydrogenolysis of 1-(α-methylbenzyl)-3-(3-chlorophenoxy)azetidine in isopropyl alcohol using the same type catalyst and conditions.

EXAMPLE 2

3-[4-(Trifluoromethyl)phenoxy]azetidine Oxalate

To 24.0 g. (0.075 mole) of 3-[4-(trifluoromethyl)-phenoxy]-1-(α-methylbenzyl)azetidine in 150 ml. of ethanol was added 0.5 g. of 20% Pd(OH)$_2$ on carbon, and the mixture was hydrogenated for five hours at 80° C. and 45 psi. The mixture was cooled, filtered, and the filtrate concentrated at reduced pressure. The residue was dissolved in ethanol and treated with oxalic acid, and the oxalate salt was recrystallized three times in ethanol. The yield was 3.0 g. (13%) and the salt melted at 176°–178° C.

Analysis: Calculated for $C_{12}H_{12}F_3NO_3$: C,46.91; H,3.94; N,4.56 Found: C,47.07; H,3.96; N,4.59

Examples 3 to 7 were prepared according to the procedure set forth in detail in Examples 1 to 2 by hydrogenolysis of the α-methylbenzyl radical attached to the azetidine nitrogen. The physical constants are shown in Table 1.

TABLE 1

H—N⟨azetidine⟩—O—⟨phenyl⟩—R

| Example | R | M.P. °C. | Salt |
|---|---|---|---|
| 3 | 2-CONH$_2$ | 173–75 | CH$_3$SO$_3$H |
| 4 | 3-CF$_3$ | 123–25 | [1]C$_6$H$_{11}$NHSO$_3$H |
| 5 | 2-CF$_3$ | 154–56 | HCl |
| 6 | 3-CONH$_2$ | 160–63 | — |
| 7 | 4-CONH$_2$ | 187–88 | (COOH)$_2$ |

[1]N—cyclohexylsulfamate

The analytical data of Examples 3 to 7 are shown in Table 2.

TABLE 2

Analytical Data on Examples 3 to 7

| Example | Empirical Formula | Calculated C | Calculated H | Calculated N | Found C | Found H | Found N |
|---|---|---|---|---|---|---|---|
| 3 | C$_{11}$H$_{16}$N$_2$O$_5$S | 45.82 | 5.59 | 9.72 | 45.48 | 5.65 | 9.45 |
| 4 | C$_{16}$H$_{23}$F$_3$N$_2$O$_4$S | 48.48 | 5.85 | 7.07 | 48.08 | 5.94 | 6.97 |
| 5 | C$_{10}$H$_{11}$ClF$_3$NO | 47.35 | 4.37 | 5.52 | 47.12 | 4.32 | 5.45 |
| 6 | C$_{10}$H$_{12}$N$_2$O$_2$ | 62.49 | 6.29 | 14.57 | 62.06 | 6.43 | 13.98 |
| 7 | C$_{12}$H$_{14}$N$_2$O$_6$ | 51.07 | 5.00 | 9.93 | 51.39 | 5.22 | 9.56 |

FORMULATION AND ADMINISTRATION

Effective quantities of any of the foregoing pharmacologically active 3-phenoxyazetidines may be administered to a living animal body, particularly humans, orally as in capsules, tablets or elixirs. The free basic amino compounds, while effective, are preferably formulated and administered in the form of their pharmaceutically acceptable non-toxic acid addition salts.

Although very small quantities of the active materials of the present invention, even as low as one milligram, are effective when minor therapy is involved or in the cases of administration to subjects having a relatively low body weight, unit dosages are usually two milligrams or above and preferably five, ten, or twenty milligrams. Five to twenty milligrams appear optimum per unit dose, while usual broader ranges appear to be one to twenty milligrams per unit dose. The active agents of the invention may be combined with other pharmacologically active agents, or with buffers, antacids or the like, for administration and the proportion of the active agent in the composition may be varied widely. It is only necessary that the active ingredient constitute an effective amount; i.e., such that a suitable effective dosage will be obtained consistent with the dosage form employed. Obviously, several unit dosage forms may be administered at about the same time.

Therapy for humans with the compounds of this invention may be initiated at daily dosages of 20 mg. of drug given three times a day before meals. Thereafter, the dosage should be adjusted to the need and response of the patient. Depending on the effectiveness and tolerance, the daily dosage may be administered as 20 mg. of drug given two times a day up to 40 mg. of drug given three times a day. The drug may be conveniently administered as 20 mg. tablets.

Examples of compositions within the preferred ranges are given as follows:

CAPSULES

Capsules of 5 mg., 10 mg., and 20 mg. of active ingredient per capsule are prepared; with the higher amounts of ingredient, reduction may be made in the amount of lactose.

| Typical blend for encapsulation | Per Capsule, mg. |
|---|---|
| Active ingredient | 5.0 |
| Lactose | 296.7 |
| Starch | 129.0 |
| Magnesium stearate | 4.3 |
| Total | 435.0 mg. |

Uniformly blend the selected active ingredient with lactose, starch and magnesium stearate and encapsulate the blend.

TABLETS

A typical formulation for a tablet containing 5.0 mg. of active ingredient per tablet follows. The formulation may be used for other strengths of active ingredient by adjustment of weight of dicalcium phosphate.

| Ingredients | Per Tablet, mg. |
|---|---|
| (1) Active ingredient | 5.0 |
| (2) Corn starch | 13.6 |
| (3) Corn starch (paste) | 3.4 |
| (4) Lactose | 79.2 |
| (5) Dicalcium phosphate | 68.0 |
| (6) Calcium stearate | 0.9 |
| Total | 170.1 mg. |

Uniformly blend 1, 2, 4 and 5. Prepare 3 as a 10 percent paste in water. Granulate the blend with the starch paste and pass the wet mass through a number eight mesh screen. The wet granulation is dried and passed through a number twelve mesh screen. The dried granules are blended with calcium stearate and compressed.

What is claimed is:

1. A process which comprises administering to a living animal body for its anorexigenic effect an effective amount of a compound selected from the group consisting of 3-phenoxyazetidines of the formula:

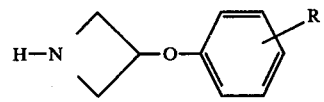

wherein R is hydrogen, aminocarbonyl or trifluoromethyl and pharmaceutically acceptable acid addition salts thereof in admixture with a pharmaceutically acceptable carrier.

2. An anticonvulsant pharmaceutical composition comprising (a) five to twenty milligrams of a compound of the formula:

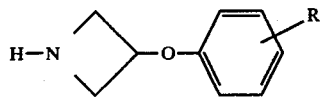

wherein;
R is hydrogen, aminocarbonyl and trifluoromethyl or a pharmaceutically acceptable acid addition salt thereof, and
(b) a pharmaceutically acceptable carrier therefor.

3. The process as defined in claim 1 wherein the compound is 3-phenoxyazetidine.

4. The process as defined in claim 1 wherein the compound is 3-(3-trifluoromethyl)phenoxyazetidine.

* * * * *